(12) United States Patent
Inagaki et al.

(10) Patent No.: US 7,109,008 B2
(45) Date of Patent: Sep. 19, 2006

(54) L-GLUTAMATE OXIDASE

(75) Inventors: Kenji Inagaki, Okayama (JP); Jiro Arima, Okayama (JP); Makoto Ashiuchi, Kochi (JP); Toshiharu Yagi, Kochi (JP); Hitoshi Kusakabe, Chiba (JP)

(73) Assignee: Yamasa Corporation, Choshi (JP)

( * ) Notice: Subject to any disclaimer, the term of this patent is extended or adjusted under 35 U.S.C. 154(b) by 290 days.

(21) Appl. No.: 10/257,398

(22) PCT Filed: Apr. 19, 2001

(86) PCT No.: PCT/JP01/03345

§ 371 (c)(1),
(2), (4) Date: Jun. 10, 2003

(87) PCT Pub. No.: WO01/79503

PCT Pub. Date: Oct. 25, 2001

(65) Prior Publication Data

US 2004/0091989 A1 May 13, 2004

(30) Foreign Application Priority Data

Apr. 19, 2000 (JP) ............................ 2000-117749
Mar. 2, 2001 (JP) ............................ 2001-57848

(51) Int. Cl.
C12N 9/02 (2006.01)
C12N 1/20 (2006.01)
C12N 15/00 (2006.01)
C12Q 1/68 (2006.01)
C12Q 1/34 (2006.01)
C12P 21/04 (2006.01)
C07H 21/04 (2006.01)

(52) U.S. Cl. ............................ 435/189; 435/4; 435/6; 435/18; 435/252.3; 435/320.1; 435/69.1; 435/71.1; 435/440; 536/23.2; 536/23.7

(58) Field of Classification Search ................ 435/189, 435/4, 6, 69.1, 71.1, 440, 252.3, 320.1, 18, 435/25; 536/23.2, 23.7
See application file for complete search history.

(56) References Cited

U.S. PATENT DOCUMENTS 4,605,615 A 8/1986 Ishikawa et al.

FOREIGN PATENT DOCUMENTS

EP 97949 1/1984

OTHER PUBLICATIONS

Kunst et al. The complete genome sequence of the gram-positive bacterium *Bacillus subtilis*. Nature. Nov. 20, 1997;390(6657):249-56.*
Kunst et al. Sequence Alignment.*
Chen et al. Sequence Alignment.*
J. Arima, et al., Journal of Biochemistry, vol. 134, No. 6, XP-002273495, pp. 805-812, "Recombinant Expression, Biochemical Characterization and Stabilization Through Proteolysis of an L-Glutamate Oxidase from Streptomyces SP. X-119-6", Dec. 2003.
Toshio Kamei et al.: "L-Glutamate oxidase from streptomyces violascens. I. Production, Isolation and some properties" Chem. Pharm. Bull., vol. 31, No. 4, pp. 1307-1314 1983.
Toshio Kamei et al.: "L-Glutamate oxidase from streptomyces violascens. II. Properties" Chem. Pharm. Bull., vol. 31, No. 10, pp. 3609-3616 1983.
Chien-Yuan Chen et al.: "A common precursor for the three subumits of L-glutamate oxidase encoded by gox gene from Streptomyces platensis NTU 3304" Canadian Journal of Microbiology, vol. 47, No. 3, pp. 269-275 Mar. 2001.
Annette Bohmer et al.: "A novel L-glutamate oxidase from Streptomyces endus" European Journal of Biochemistry, vol. 182, No. 2, pp. 327-332 1989.
Hitoshi Kusakabe et al.: "Purification and properties of a new enzyme, L-glutamate oxidase, from Streptomyces sp. X-119-6 grown on wheat bran" Agricultural and Biological Chemistry, vol. 47, No. 6, pp. 1323-1328 1983.

* cited by examiner

Primary Examiner—Ponnathapu Achutamurthy
Assistant Examiner—Yong D. Pak
(74) Attorney, Agent, or Firm—Oblon, Spivak, McClelland, Maier & Neustadt, P.C.

(57) ABSTRACT

The present invention provides a novel L-glutamate oxidase, a gene encoding the enzyme, and a method for producing the enzyme. By use of a gene encoding the enzyme, L-glutamate oxidase can be readily prepared at low costs through a recombinant DNA technique. The novel L-glutamate oxidase has the following physicochemical properties:

(A) action: catalyzing the following reaction:

$$L\text{-glutamic acid} + O_2 + H_2O \rightarrow \alpha\text{-ketoglutaric acid} + H_2O_2 + NH_3;$$

(B) substrate specificity: being specific to L-glutamic acid;

(C) molecular weight and subunit structure: molecular weight as determined through SDS-polyacrylamide gel electrophoresis of 70,000±6,000, molecular weight as determined through gel filtration of 140,000±10,000, and being a dimer formed of the same subunits having a molecular weight of 70,000±6,000;

(D) optimum pH: around pH 6.0 to 8.5;

(E) heat stability: being stable up to 60° C. at a pH of 7.4 for 30 minutes; and (F) coenzyme: flavin adenine dinucleotide (FAD).

13 Claims, 5 Drawing Sheets

Fig. 1

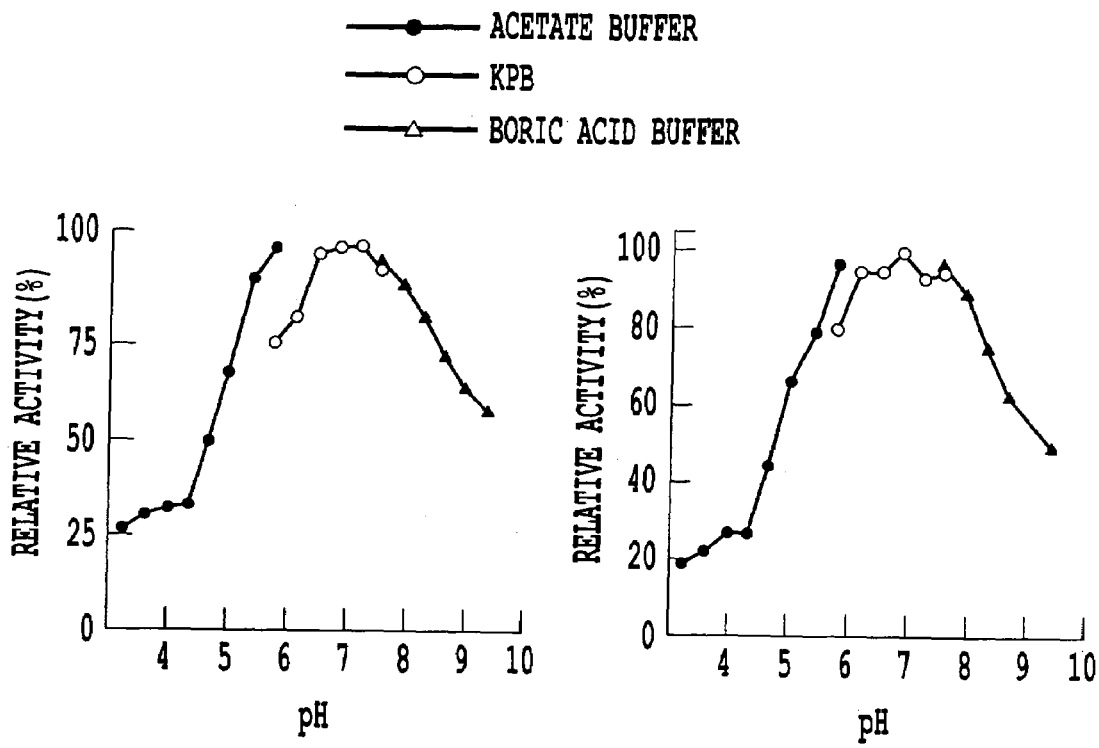
*Fig. 6C*
*Fig. 6D*
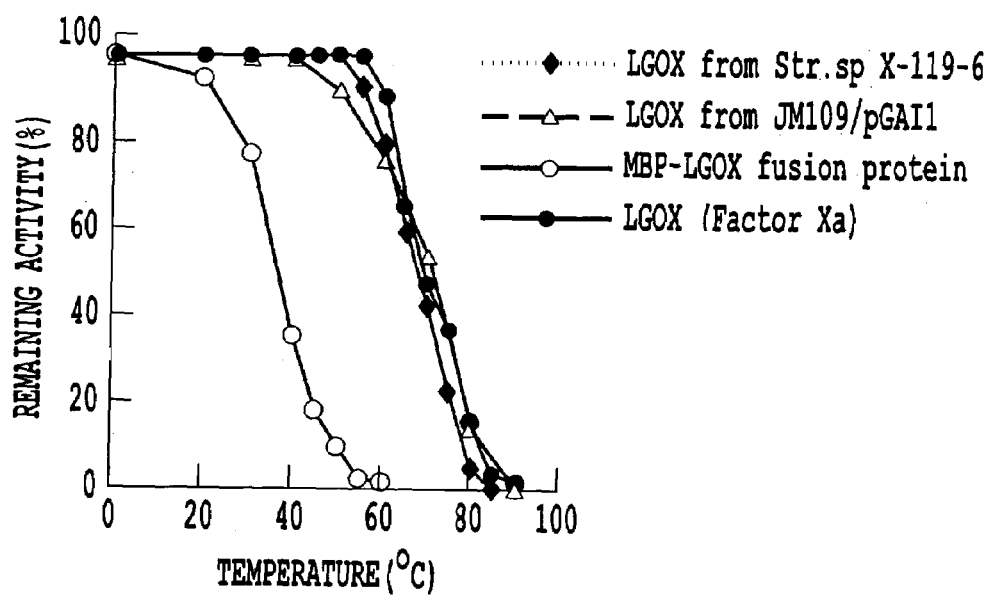
*Fig. 7*

L-GLUTAMATE OXIDASE

TECHNICAL FIELD

The present invention relates to a novel L-glutamate oxidase, a gene encoding the enzyme, and a method for producing the enzyme.

BACKGROUND ART

L-Glutamate oxidase is an enzyme which catalyzes the following reaction:

L-glutamic acid+$O_2$+$H_2O$→α-ketoglutaric acid+ $H_2O_2$ +$NH_3$.

The known species of L-Glutamate oxidase include those obtained through isolation and purification from *Streptomyces* sp. X-119-6, *Streptomyces violascens*, and *Streptomyces endus* (Agric. Biol. Chem., 47, 1323–1328 (1983), Chem. Pharm. Bull., 31, 1307–1314 (1983), Chem. Pharm. Bull., 31, 3609–3616 (1983), Eur. J. Biochem., 182, 327–332 (1989)).

These L-glutamate oxidases have the following characteristics in common: (1) being produced from microorganisms belonging to genus *Streptomyces*; (2) remarkably high substrate specificity to L-glutamic acid; (3) comparatively stable under variations in temperature and pH; and (4) being a flavin enzyme requiring FAD as a coenzyme. However, these glutamate oxidases significantly differ in molecular weight depending on the microorganisms from which they have been obtained. For example, an L-glutamate oxidase derived from Streptomyces sp. X-119-6 has a molecular weight of about 140,000 (heteromer: $\alpha_2\beta_2\gamma_2$, α=about 44,000; β=about 16,000; and γ=about 9,000); that derived from *Streptomyces violascens* has a molecular weight of about 62,000 (monomer); and that derived from *Streptomyces endus* has a molecular weight of about 90,000 (dimer).

L-Glutamic acid, which is a predominant ingredient that imparts a flavor (umami) to food, is added to foods, inter alia processed foods, and such use amounts to about 1,000,000 tons per year. Since the L-glutamic acid content of foods can be readily determined by means of a kit or a sensor employing L-glutamate oxidase, this enzyme is now indispensable in the field of compositional analysis of foods.

Meanwhile, in recent years, in the field of cerebral nerve science, attempts to analyze L-glutamic acid—an intracerebral nuerotransmitter—have been energetically pursued by use of a microdialysis and a microsensor in combination. Most enzymes employed in the sensor are L-glutamate oxidases. Thus, the enzymes have become of more and more importance.

However, production processes of L-glutamate oxidase are not necessarily simple. For example, the L-glutamate oxidase derived from Streptomyces sp. X-119-6 is difficult to produce through liquid culturing, and therefore, solid culturing is employed to produce the enzyme.

Therefore, if a gene encoding L-glutamate oxidase can be obtained by cloning, L-glutamate oxidase can be readily prepared through a recombinant DNA technique, and new characteristics which native L-glutamate oxidase does not possess can be imparted to the prepared L-glutamate oxidase. However, hitherto, neither analysis of a gene encoding L-glutamate oxidase nor the amino acid sequence of the enzyme has been reported.

DISCLOSURE OF THE INVENTION

The present inventors have determined an N-terminal amino acid sequence of a subunit of the L-glutamate oxidase derived from *Streptomyces* sp. X-119-6, have produced primers on the basis of the sequence, and have carried out screening of a genomic DNA library, to thereby find a gene encoding a protein having an estimated molecular weight of about 76,000. The inventors have purified an enzyme produced through transformation of *E. coli*. by the gene and culturing, to thereby isolate a purified L-glutamate oxidase. The inventors have found, surprisingly, that the thus-isolated L-glutamate oxidase is formed of two subunits which are identical and have a molecular weight of about 70 kDa each (differing from conventionally reported features) and that the thus-isolated L-glutamate oxidase maintains L-glutamate oxidase activity although it does not have $\alpha_2\beta_2\gamma_2$ subunit conventionally reported. The present invention has been accomplished on the basis of these findings.

Accordingly, the present invention is drawn to a novel L-glutamate oxidase having the following physicochemical properties:

(A) action: catalyzing the following reaction:

L-glutamic acid+$O_2$+$H_2O$→α-ketoglutaric acid+ $H_2O_2$ +$NH_3$;

(B) substrate specificity: being specific to L-glutamic acid;

(C) molecular weight and subunit structure: molecular weight as determined through SDS-polyacrylamide electrophoresis of 70,000±6,000, molecular weight as determined through gel filtration of 140,000±10,000, and being a dimer formed of two identical subunits having a molecular weight of 70,000±6,000;

(D) optimum pH: around pH 6.0 to 8.5;

(E) heat stability: being stable up to 60° C. at a pH of 7.4 for 30 minutes; and (F) coenzyme: flavin adenine dinucleotide (FAD).

The present invention is also directed to an L-glutamate oxidase having an amino acid sequence represented by SEQ ID NO: 1 or a corresponding amino acid sequence in which one or more amino acid residues have been deleted, substituted, inserted, or added.

The present invention is also directed to an L-glutamate oxidase gene encoding the amino acid sequence.

The present invention is also directed to an L-glutamate oxidase gene having a nucleotide sequence represented by SEQ ID NO: 2 or a corresponding nucleotide sequence in which one or more nucleotides have been deleted, substituted, inserted, or added.

The present invention is directed to a method for producing L-glutamate oxidase, comprising the steps of transforming a host microorganism by use of the expression vector which has been prepared by inserting any of the aforementioned DNA fragments into a plasmid; culturing the resultant transformant, to thereby produce L-glutamate oxidase; and isolating the L-glutamate oxidase from the cultured product and purifying the product.

BRIEF DESCRIPTION OF THE DRAWINGS

FIG. 1 shows results of analysis of the nucleotide sequence and amino acid sequence of L-glutamate oxidase, wherein the double line denotes a signal peptide and the box denotes an FAD binding site.

In FIG. 6, solid black circles represent relative activities determined by use of an acetate buffer (pH 3.5–6.0); white circles represent those determined by use of a potassium phosphate buffer (pH 6.0 to 8.0); and triangles represent those determined by use of a borate buffer (pH 8.0 to 10.0).

FIG. 7 shows heat stability of L-glutamate oxidases according to the present invention and that of L-glutamate oxidase derived from *Streptomyces* sp. X-119-6 strain. In FIG. 7, rhombuses represent *Streptomyces* sp. X-119-6 strain-derived LGOX; triangles represent *E. coli* JM109/pGAI1-derived LGOX; white circles represent *E. coli* JM109/pGOX mal1-derived MBP-LGOX fusion protein; and solid black circles represent *E. coli* JM109/pGOX mal1-derived LGOX (factor Xa-treated).

BEST MODES FOR CARRYING OUT THE INVENTION

Figure 2:
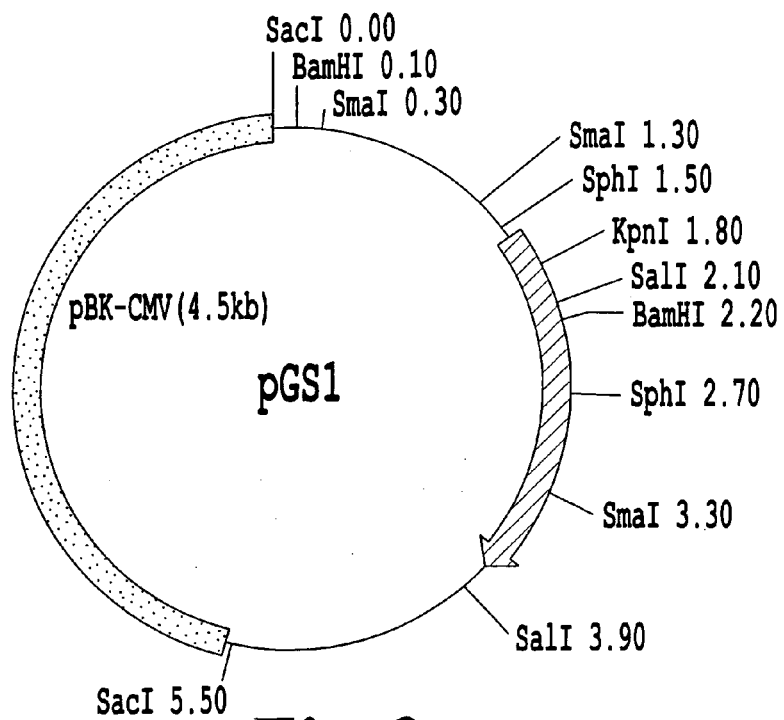
FIG. 2 shows the structure of plasmid pGS1.

The novel L-glutamate oxidase of the present invention has the following physicochemical properties:

(A) action: catalyzing the following reaction:

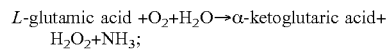

L-glutamic acid $+O_2+H_2O \rightarrow$ α-ketoglutaric acid$+H_2O_2+NH_3$;

(B) substrate specificity: being specific to L-glutamic acid;

(C) molecular weight and subunit structure: molecular weight as determined through SDS-polyacrylamide electrophoresis of 70,000±6,000, molecular weight as determined through gel filtration of 140,000±10,000, and being a dimer formed of two identical subunits having a molecular weight of 70,000±6,000;

(D) optimum pH: around pH 6.0 to 8.5;

(E) heat stability: being stable up to 60° C. at a pH of 7.4 for 30 minutes; and (F) coenzyme: flavin adenine dinucleotide (FAD).

The L-glutamate oxidase of the present invention has an amino acid sequence represented by SEQ ID NO: 1. However, the amino acid sequence of the invention is not limited to the sequence represented by SEQ ID NO: 1, so long as L-glutamate oxidase activity is conserved, and corresponding amino acid sequences in which one or more amino acid residues have been deleted, substituted, inserted, or added also fall within the scope of the invention. Examples of such amino acid sequences include those in which N-terminal alanine has been substituted by methionine; and those in which methionine has been added to N-terminal alanine. In addition, enzymes having a homology of at least 90% to the amino acid sequence represented by SEQ ID NO: 1 fall within the definition of the L-glutamate oxidase of the present invention, so long as L-glutamate oxidase activity is conserved.

The aforementioned enzyme of the present invention can be produced by obtaining a gene encoding the L-glutamate oxidase from Streptomyces sp. X-119-6; preparing a recombination vector by use of the gene; transforming host cells by use of the recombination vector; culturing the resultant transformant; and collecting L-glutamate oxidase from the culture product. Although no particular limitation is imposed on the host cells, *E. coli* is preferred.

In the present invention, a gene encoding the SEQ ID NO: 1 amino acid or a variant thereof in which an amino acid residue or amino acid residues have been deleted, substituted, inserted, or added can be employed as the gene encoding L-glutamate oxidase. Preferably, the gene has a nucleotide sequence represented by SEQ ID NO: 2 or a corresponding nucleotide sequence in which one or more nucleotides have been deleted, substituted, inserted, or added. Genes having a homology of at least 90% to the nucleotide sequence represented by SEQ ID NO: 2 fall within the definition of the gene of the present invention.

Figure 1:
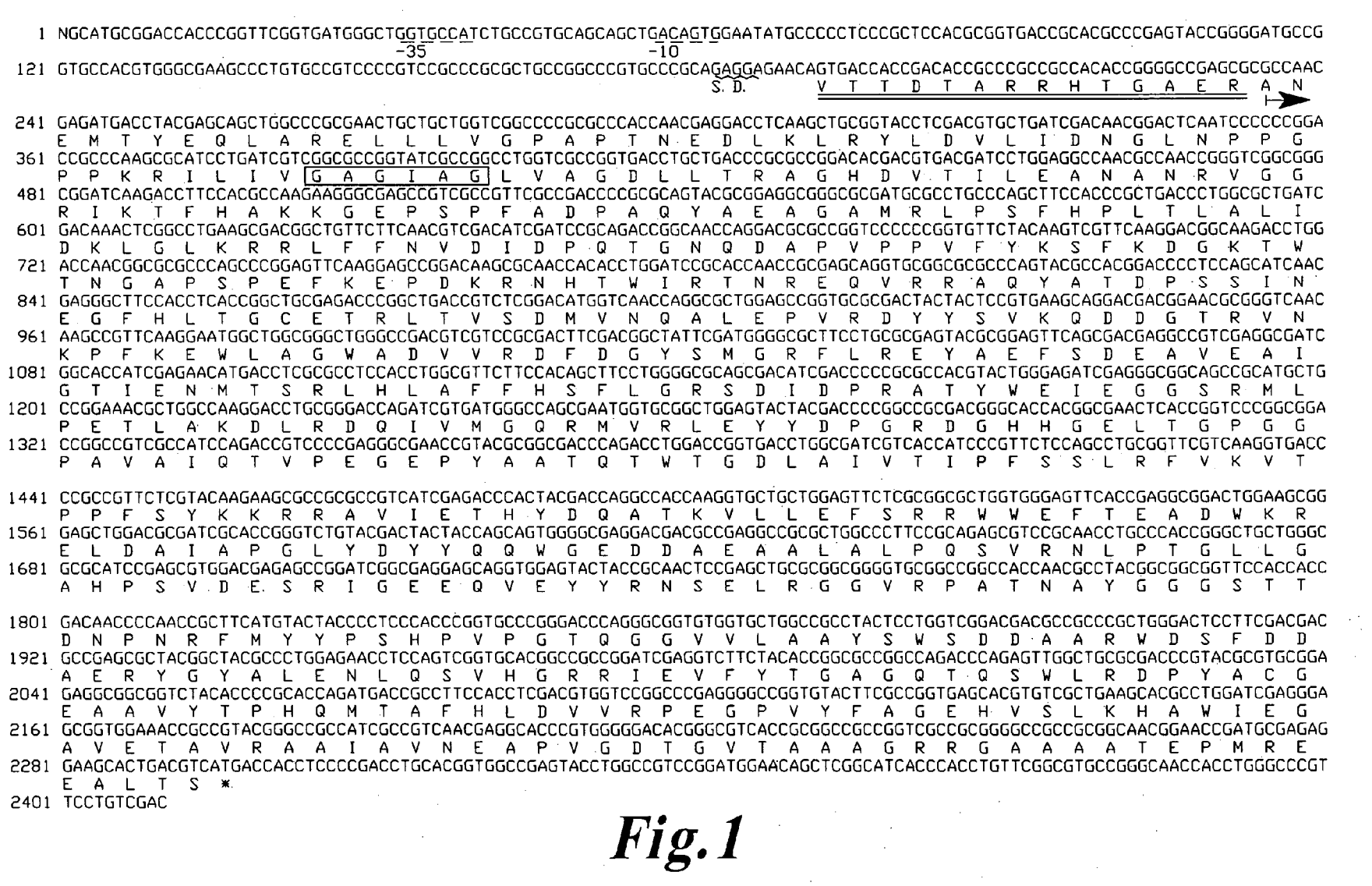

The gene of the present invention encoding L-glutamate oxidase is represented by base Nos. of 235 to 2,295 shown in FIG. 1. Alternatively, a DNA fragment which can be hybridized with a DNA fragment of the above gene under stringent conditions may also be employed. As used herein, the expression "can be hybridized with a DNA fragment under stringent conditions" refers to the ability to attain hybridization through hybridization reaction at 60° C. for about 20 hours by use of a solution containing 5×SSC (1×SSC: sodium chloride (8.76 g) and sodium citrate (4.41 g) dissolved in water (1 L)), 0.1% w/v N-lauroylsarcosine sodium salt, 0.02% w/v SDS, and 0.5% w/v blocking reagent.

According to the present invention, a DNA fragment which further contains, on the upstream side of the gene encoding L-glutamate oxidase, a sequence encoding a signal peptide and/or the SD (Shine-Dalgarno) sequence may also be employed. Through employment of such a DNA fragment, an enzyme can be produced in an increased amount, and the produced enzyme can be purified more easily, depending on the host cells employed. With reference to FIG. 1, an example of such DNA fragments is represented by at least base Nos. 183 to 2,295. This DNA fragment contains the SD sequence and a sequence coding for signal peptide formed of 14 amino acid residues.

In the present invention, any known technique can be employed for the preparation of DNA fragments, including cloning of a target gene obtained from chromosomal DNA of a microorganism; preparation of an expression vector by use of a cloned DNA fragment; and production of L-glutamate oxidase by use of the expression vector.

Specifically, chromosomal DNA is obtained, through a known extraction method, from *Actinomyces* belonging to *Streptomyces*, and the thus-obtained DNA is integrated into a plasmid or a phage vector, preferably a plasmid, to thereby prepare a DNA library of a microorganism such as *E. coli* or *Actinomyces*. Any plasmids can be employed as plasmids into which the DNA is to be integrated, so long as the plasmids can be replicated and maintained in the host. Examples of the plasmids include those of *E. coli* or *Actinomyces*. Specific examples of *E. coli* plasmids include pBR322 [Gene, 2, 95 (1977)], pBR325 [Gene, 4, 121 (1978)], and pUC13 [Gene, 19, 259 (1982)], and specific examples of *Actinomyces* plasmids include pIJ61 [Gene, 20, 51 (1982)], and pIJ702 [J. Gen. Microbiol., 129, 2703 (1983)].

Examples of methods for integrating chromosomal DNA into a plasmid vector include any appropriate methods known per se (e.g., disclosed in Maniatis, T. et al., Molecular Cloning, Cold Spring Harbor Laboratory, 239, 1982 and Hopwood, D. A. et al., Genetic Manipulation of *Streptomyces*, A Laboratory Manual, The John Innes Foundation, 1985).

Next, the thus-obtained plasmid vector is transferred into a host. Examples of the host include, but are not limited to, *E. coli* and actinomycetes. Use of *E. coli* is preferred, because it provides excellent productivity of the novel L-glutamate oxidase of the present invention. Examples of *E. coli* include *Escherichia coli* K12 DH1 [Pro., Natl. Acad. Sci., U.S.A. 60, 160 (1968)], *Escherichia coli* JM103 [Nucl. Acids. Res., 9, 309 (1981)], *Escherichia coli* JA221 [J. Mol. Biol., 120, 517 (1978)], *Escherichia coli* HB101 [J. Mol. Biol., 41, 459 (1969)], and *Escherichia coli* C600 [Genetics, 39, 440 (1954)]. Examples of actinomycetes include *Streptomyces lividans* TK64 and derivatives thereof [Genetics Manipulation of *Streptomyces*, A Laboratory Manual].

Transformation of the host with a plasmid may be performed through any appropriate method known per se. For example, when *E. coli* is used as a host, employable methods include the calcium chloride method and the calcium chloride/rubidium chloride method described in, for example, Molecular Cloning [Cold Spring Harbor Laboratory, 239 (1982)]. When an actinomycetes is used as a host, the protoplast method described in "Genetics Manipulation of *Streptomyces*, A Laboratory Manual" may be performed.

In a manner described above, a DNA library of *E. coli* or actinomycetes is obtained, and through use of the DNA library, cloning of an L-glutamate oxidase gene is performed. The cloning may be performed through any appropriate method known per se. For example, there may be employed a method making use of functional expression achieved by use of 4-aminoantipyrin, phenol, and peroxidase to thereby develop color in the presence of hydrogen peroxide. Alternatively, there may be employed colony hybridization using, as a probe, an oligonucleotide chemically synthesized on the basis of an amino acid sequence [Molecular Cloning, Cold Spring Harbor Laboratory, (1982)].

According to needs, the thus-cloned gene capable of encoding L-glutamate oxidase may be sub-cloned into a plasmid such as pBR322, pUC12, pUC13, pUC18, pUC19, pUC118, pUC119, pIJ702, pIJ61, pIJ101, pIJ486, or pIJ425.

The nucleotide sequence of the obtained DNA is determined through any appropriate method known per se, such as the Maxam-Gilbert method [Pro. Natl. Acad. Sci., U.S.A. 74, 560 (1977)], the dideoxy method [Nucl. Acids. Res., 9, 309 (1981)], or the deaza method [Nucl. Acids. Res., 14, 1319(1986)].

Next, the amino acid sequence deduced from the nucleotide sequence of the obtained DNA is compared with, for example, the previously analyzed N-terminal amino acid sequence of a known L-glutamate oxidase, to thereby confirm the presence of a DNA fragment encoding L-glutamate oxidase. When this step reveals that not the entire region of the L-glutamate oxidase gene is covered, colony hybridization or PCR is performed through use, as a probe, of a fragment of the previously cloned DNA for additional cloning, whereby DNA coding for the entire region of the L-glutamate oxidase gene is obtained.

L-Glutamate oxidase may be produced through the following method. That is, the above-mentioned fragment of cloned DNA is inserted into a known plasmid harboring a promoter, etc., to thereby yield an expression vector. Subsequently, microorganisms (such as actinomyces and *E. coli*) that have been transformed with the expression vector are incubated through use of any appropriate method known per se for production of L-glutamate oxidase in the culture product or in cells. Alternatively, through a routine method L-glutamate oxidase may be produced in the form of a fusion protein, which is a protein fused with, for example, maltose binding protein (MBP).

Transformants may be incubated through any appropriate method known per se. For example, there may be employed a culture medium containing a carbon source such as glucose, glycerol, dextrin, sucrose, starch, or molasses; a nitrogen source such as corn steep liquor, cotton seed powder, raw soybean powder, pepton, or yeast extract; and inorganic nitrogen compounds, including a variety of ammonium salts and nitrates; and when needed, diverse inorganic salt compounds capable of releasing phosphate ions, magnesium ions, sodium ions, potassium ions, chlorine ions, or sulfate ions; and further, micro-elements required for growth, a variety of defoamers, etc. The incubation temperature is typically about 10 to about 50° C., preferably about 20 to about 40° C. The incubation time is about 1 to 96 hours, preferably about 10 to 72 hours. If necessary, incubation is performed under aeration or stirring.

In the case where expression of the L-glutamate oxidase gene must be induced during incubation, a method which is generally used for the promoter employed is performed, to thereby induce expression of the gene. For example, when the promoter employed is an lac promoter, a tac promoter, or a Taq promoter, in the midterm of incubation, an appropriate amount of an expression inducer, isopropyl-β-D-thiogalactopyranoside (hereinafter abbreviated as IPTG), is added.

From the thus-prepared culture product, cells are recovered through a technique such as membrane separation or centrifugal separation.

In order to isolate L-glutamate oxidase from the recovered cells and purify the enzyme, a variety of methods which are generally employed for isolation and purification of enzymes may be appropriately combined. For example, the recovered cells are suspended in an appropriate buffer, and the cells are physically disrupted through ultrasonication, by use of a French press, or by similar means. Alternatively, the cells are subjected to an enzymatic lysis treatment, such as lysozyme treatment, and then cell debris is removed through centrifugation, to thereby prepare a cell-free extract. If necessary, the extract is further subjected to any of thermal treatment, ammonium sulfate salting-out treatment, dialysis, treatment with a solvent such as ethanol, and a variety of chromatography techniques, which may be performed singly or in combination, whereby L-glutamate oxidase can be isolated and purified.

EXAMPLES

The present invention will next be described in detail by way of examples, which should not be construed as limiting the invention. All the methods described in the following Examples, such as preparation of DNA, cleaving DNA with a restriction enzyme, ligation of DNA, and transformation of *E. coli*, were performed in accordance with "Molecular Cloning, A Laboratory Manual, Second Edition" (edited by Sambrook et al., Cold Spring Harbor Laboratory, Cold Spring Harbor, N.Y. (1989)).

Example 1

Analysis of a Gene Encoding L-Glutamate Oxidase (1) Probe

L-glutamate oxidase derived from *Streptomyces* sp. X-119-6 (ATCC 39343) is constituted by three subunits. In the present invention, the following probes (probe α and probe γ) were used. The probes were designed on the basis of the N-terminal amino acid sequences of α and γ subunits, which had been previously analyzed (α subunit: Ala-Asn-Glu-Met-Thr-Tyr-Glu . . . , γ subunit: Ala-Ile-Val-Thr-Ile-Pro-Phe . . . ).
Probe α: 5'-AACGAGATGAC(C or G)TACGAGCA-3'
(20 mers, 2 probes, (G+C) content=50%, Tm=60° C.)
Probe γ: 5'-GC(C or G)ATCGT(C or G)AC(C or G)ATC-CC(C or G)TT-3'
(20 mers, 16 probes, (G+C) content=50%, Tm=64° C.)

(2) Cloning

A chromosomal DNA derived from *Streptomyces* sp. X-119-6 (ATCC 39343) was prepared through a conventional method, and the DNA was cleaved with BamHI. Subsequently, the resultant DNA fragments were subjected to agarose gel electrophoresis, to thereby obtain DNA fragments having size of about 2 kb. A DNA library was constructed by use of the DNA fragments, pUC19 (Takara Shuzo Co., Ltd.) as a vector, and *E. coli* (MV1184) (Takara Shuzo Co., Ltd.) as a host. The recombinant was subjected to colony hybridization by use of probe α. The hybridization was performed at 55° C. on a membrane, and the membrane was sequentially washed at 58° C., 62° C., and 64° C. Each washing was performed for ten minutes. The thus-obtained membrane was autoradiographed, and subsequently, about 5,000 strains were screened, to thereby obtain 12 strains forming positive colonies.

Plasmids were extracted from the thus-obtained 12 strains which form positive colonies. The inserted DNA portion was cleaved from the plasmids by use of BamHI, followed by southern hybridization, whereby plasmids of five strains of strong signal were obtained.

Each insert DNA was confirmed to have a size of 2.3 kb. A restriction map of the insert DNA revealed the presence of unique restriction sites (BamHI (0 kb), SmaI (0.15 kb), StyI (1.05 kb), SphI (1.5 kb), KpnI (1.76 kb), SalI (2.2 kb), and BamHI (2.3 kb) as viewed from the upstream side of insertion).

In order to identify the position in the insert DNA at which probe α is hybridized, the thus-obtained plasmids were cleaved with restriction enzymes (other than SalI and SmaI) in the map, and the respective digested fragments were subjected to southern hybridization.

Southern hybridization analysis revealed that probe α was hybridized at a position between SphI and KpnI of the insert DNA.

With reference to an N-terminal amino acid sequence of the α subunit of L-glutamate oxidase derived from *Streptomyces* sp. X-119-6 (ATCC 39343), sequencing of the insert DNA confirmed the presence of a signal peptide constituted by 14 amino acid residues, a valine residue GTG (which is considered a translation initiation site) at a position 15 amino acid residues upstream of the N-terminal, and a sequence having high homology to an SD sequence at a position 6 bp upstream of the valine residue.

A previous analysis had revealed that the α subunit of L-glutamate oxidase derived from *Streptomyces* sp. X-119-6 (ATCC 39343) has a molecular weight of about 40,000 and a size of about 1 kb. However, the insert DNA having a size of 2.3 kb was found to have a nucleotide sequence of only 582 bp (i.e., about 60% of the α subunit) from the valine residue GTG, which is considered a translation initiation site.

Thus, in order to carry out cloning of the full length L-glutamate oxidase gene, the chromosomal DNA is cleaved with SacI, followed by agarose gel electrophoresis for collection of DNA fragments. A 6 kb DNA fragment resulting from the excision with SacI was ligated to λ ZAP Express Phage DNA (product of Toyobo) employed as a vector, followed by packaging, whereby a library was constructed. Subsequently, *E. coli* XL1 blue MRF1 (product of Toyobo) was infected with the library for formation of plaques. The plaques were directly employed in blotting, and through plaque hybridization using, as a probe, a KpnI-BamHI fragment (about 0.5 kb) in the 2.3 kb BamHI fragment, two plaques having intense signals were obtained.

The vector portion of a positive plaque thus-obtained was rescued as to pBK-CMV through the single-clone excision method (Nucleic Acids Res., 15, 7583–7600 (1988)), then subjected to plasmid extraction. The obtained plasmid, named pGS1 (FIG. 2), was digested with restriction enzymes, and the insert fragments were confirmed through agarose electrophoresis, followed by southern hybridization analysis by use of probes α and γ. Also, mapping of restriction enzymes of the inserted SacI fragment through a conventional method revealed the presence of the following restriction enzymes in the listed order from the upstream side of insertion: SacI (0 kb), BamHI (0.1 kb), SmaI (0.3 kb), SmaI (1.3 kb), SphI (1.5 kb), KpnI (1.8 kb), SalI (2.1 kb), BamHI (2.2 kb), SphI (2.7 kb), SmaI (3.3 kb), SalI (3.9 kb), SmaI (4.2 kb), and SacI (5.5 kb).

The southern hybridization revealed that probe γ is also hybridized to the downstream of probe α, suggesting high possibility of the full length L-glutamate oxidase gene being contained; therefore, sequencing was performed, so as to analyze the open reading frame (ORF) of the L-glutamate oxidase gene.

As a result of analysis, the nucleotide sequence of about 2400 bp of the insert fragment (from the SphI site present at the position of 1.5 kb in the insert fragment to the SalI site at the position of 3.9 kb) was identified, and the sequence has an initiation codon GTG and a 2103 bp ORF coding for 701 amino acid residues (FIG. 1). However, in consideration of the amino acid sequence of the N-terminal of subunit α of L-glutamate oxidase derived from *Streptomyces* sp. X-119-6 (ATCC 39343) being Ala-Asn-Glu-Met-Thr-Tyr-, degree of hydrophobicity of amino acid residues, and other factors, the 14 amino acid residues counting from the N-terminal of the protein encoded by the above-mentioned OFR are considered to correspond to a signal peptide, and the amino acid sequence of the L-glutamate oxidase of the present invention is considered to start from the 15th base, alanine, from the N-terminal.

The molecular weight of the protein of interest as calculated from the present gene was found to be 76,359 (excepting the signal peptide). This value is slightly larger than the previously reported total molecular weight (about 70,000; α subunit: about 44,000, β subunit: about 16,000, and γ subunit: about 9,000) of the three subunits of L-glutamate oxidase derived from *Streptomyces* sp. X-119-6 (ATCC 39343)

Example 2

Production of L-Glutamate Oxidase by use of *E. coli* (1)

The L-glutamate oxidase gene ORF was amplified through PCR by use of the following two primers (A) and (B) (purchased from Pharmacia) and, as a DNA sample, plasmid pGS1 containing a full-length L-glutamate oxidase gene.

```
Primer (A):  5'-CCACACCGGGGCCGAATTCATGAACCGAGAT-3'

Primer (B):  5'-AGGTACTCGGCCACCCTGCAGGTC-3'
```

Amplification of the L-glutamate oxidase gene through PCR was performed by use of a GeneAmp PCR System 2400 (product of Perkin-Elmer Cetus Instrument) through 25 cycles of treatment, each cycle consisting of thermal denaturation (96° C., 10 seconds), annealing (55° C., 30 seconds), and polymerization (60° C., 120 seconds) of 50 μL reaction mixture which contained 10×PCR buffer (5 μL), 25 mM $MgCl_2$ (5 μL), dNTP (8 μL), primer DNAs (A) and (B) (10 pmol each), the DNA sample (about 0.5 μg), and LA Taq DNA Polymerase (product of Takara Shuzo Co., Ltd.).

After amplification of the gene, a 3M sodium acetate solution was added to the reaction mixture, in an amount of one-tenth the volume of the reaction mixture. Subsequently, ethanol was added thereto in an amount 2.5 times the volume of the reaction mixture, to thereby precipitate DNA. The precipitated DNA was treated with restriction enzymes EcoRI and PstI, the obtained DNA fragments were subjected to agarose gel electrophoresis, and a DNA fragment having a size of about 2 kb was isolated. By use of a DNA Ligation Kit Ver. 1 (product of Takara Shuzo Co., Ltd.), the DNA fragment was ligated to plasmid pMal-c2 (product of New England Biolabs), which had also been treated with restriction enzymes EcoRI and PstI and then with alkaline phosphatase. *E. coli* JM109 (product of Takara Shuzo Co., Ltd.) was transformed by use of the ligation mixture. From the obtained ampicillin-resistant transformants, plasmid pGOX-mal1 was isolated.

Figure 3:
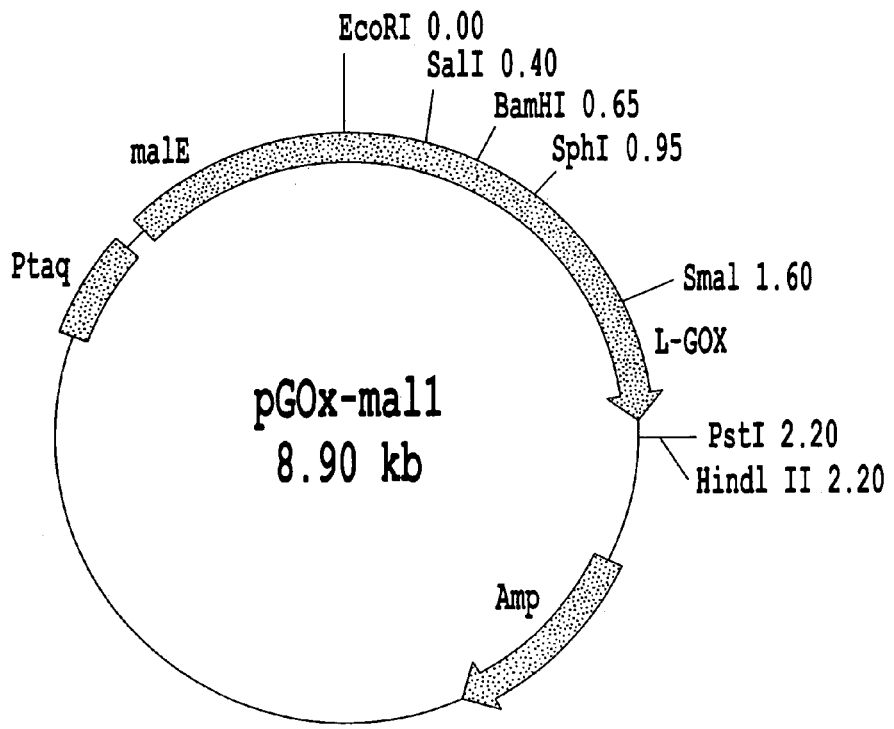
FIG. 3 shows the structure of plasmid pGOX-mal1, wherein L-GOX represents an L-glutamate oxidase gene.

The plasmid pGOX-mal1 has a Taq promoter and a maltose binding protein (MBP) gene inserted at a position upstream of the multicloning site thereof. In accordance with the open reading frame of a gene encoding MBP, the L-glutamate oxidase gene (ORF) derived from *Streptomyces* sp. X-119-6 (ATCC 39343) (from which 14 amino acids of the N-terminal signal peptide have been deleted) has been introduced into pGOX-mal1. Therefore, when the plasmid pGOX-malls is expressed in *E. coli*, a fused protein of L-gultamate oxidase and MBP can be produced (FIG. 3).

*E. coli* JM109 was transformed by use of the plasmid pGOX-mal1, and the obtained transformant was inoculated into 2×TY medium (5 mL) containing 50 μg/mL ampicillin, for shaking-culture at 30° C. for about 12 hours. Subsequently, the culture product was inoculated into 2×TY medium (1 L) containing 20 g/L glucose, and then subjected by shaking culturing at 24° C. for about 24 hours. IPTG was added to the culture product, and the resultant mixture was cultured at the same temperature for about a further 24 hours. After completion of culturing, L-gultamate oxidase was isolated and purified according to the following purification method.

Purification Method
(1) Collection, washing, and ultrasonication (100 W×15 minutes×2 times)
↓ (20 mM potassium phosphate buffer containing 100 mM NaCl)
(2) 20 to 80% Ammonium sulfate precipitation and dialysis
↓ (20 mM potassium phosphate buffer containing 100 mM NaCl)
(3) Ion exchange chromatography (stepwise elution by use of DEAE-Toyopearl 650M and 20 mM potassium phosphate buffer containing 100 to 300 mM NaCl)
↓
Condensation (by use of ammonium sulfate) and dialysis
↓ (20 mM potassium phosphate buffer containing 100 mM NaCl)
(4) Addition of Factor Xa (Product of New England Biolabs) in an amount of one-thousandth (w/w) the weight of the total proteins and maintenance at 4° C. for one day to several weeks for cleaving L-glutamate oxidase from fusion protein
↓
Confirmation of Cleavage by Use of SDS-polyacrylamide Gel Electrophoresis
↓
(5) Ion exchange chromatography (gradient elution by use of DEAE-Toyopearl 650M and 20 mM potassium phosphate buffer containing 100 to 200 mM NaCl, or by use of Q-Sepharose and 20 mM potassium phosphate buffer containing 200 to 400 mM NaCl)

TABLE 1

|  | Proteins (mg) | Activity (U) | Specific activity (U/mg protein) | Purity (fold) | Yield (%) |
| --- | --- | --- | --- | --- | --- |
| Crude enzyme solution | 1117 | 2706 | 2.42 | 1 | 100 |
| Redissolved solution after ammonium sulfate precipitation | 957.2 | 2614 | 2.73 | 1.13 | 96.6 |
| Solution after 1st ion exchange chromatography (before treatment with factor Xa) | 136.9 | 2229 | 16.3 | 6.74 | 82.4 |
| Solution after 2nd ion exchange chromatography (after treatment with factor Xa) | 28.8 | 961.8 | 33.4 | 13.8 | 35.5 |

The L-glutamate oxidase activity in the context of the present invention is measured and calculated in the following manner.

(Method of Measurement of the L-glutamate Oxidase Activity and Calculation of the Unit)

1M Potassium phosphate buffer (pH 7.0) (20 μL) was mixed with 4-aminoantipyrine (10 mg/mL) (10 μL), N-ethyl-N-(2-hydroxy-3-sulfopropyl)-m-toluidine (10 mg/mL) (10 μL), peroxidase (1 U/μL) (4 μL), 100 mM L-glutamic acid (20 μL), and sterilized water (116 μL), and the resultant mixture was pre-incubated at 37° C. for 5 minutes. A sample (20 μL) was added thereto, and the mixture was allowed to react at 37° C. for a predetermined time. After completion of reaction, absorbance of the resultant sample mixture was measured at 555 nm. By use of a calibration curve of absorbance vs. hydrogen peroxide amount, which had been prepared in advance, the amount of hydrogen peroxide was determined. One unit of enzyme activity is defined by the amount of the enzyme capable of producing 1 μmole hydrogen peroxide at 37° C. for one minute.

Example 3

Production of L-glutamate Oxidase by use of *E. coli* (2)

The L-glutamate oxidase gene was amplified by use of an LA-PCR kit (product of Takara Shuzo Co., Ltd.), the following two primers (C) and (D), which were produced on the basis of the ORF nucleotide sequence obtained through the above analysis, and chromosomal DNA derived from *Streptomyces* sp. X-119-6 (ATCC 39343) serving as a template.

```
Primer (C): 5'-GCGCCATGGAGGAATTCGCGCATGAACGAGATGACCTACGAGCAGCTGGCCCGC-3'
Primer (D): 5'-GCGAAGCTTGATCATGACGTCAGTGCTTCCTCTCGCATC-3'
```

Amplification of the L-glutamate oxidase gene by use of the LA-PCR kit was performed by means of a PCR Thermal Cycler (product of Takara Shuzo Co., Ltd.) through cycles of treatment, each cycle consisting of thermal denaturation (94° C.), annealing (68° C.), and elongation (68° C.) of GC buffer I·II solution (included in the LA-PCR Kit) containing dNTP, LA Tag, a template DNA (genomic DNA treated with SacI), and the primers (C) and (D).

After amplification of the gene, the reaction mixture was treated with a mixture of phenol and chloroform (1:1), and an aqueous fraction thus obtained was mixed with ethanol, to thereby cause DNA to precipitate. The precipitated DNA was subjected to agarose gel electrophoresis, whereby a DNA fragment having a size of about 2 kb was isolated. The DNA fragment was cleaved with restriction enzymes NcoI and HindIII, and the obtained DNA fragments were ligated, by use of T4 DNA ligase, to plasmid pTrc99A (product of Pharmacia Biotech Co.), which had also been digested with restriction enzymes NcoI and HindIII. *E. coli* JM109 (product of Takara Shuzo Co., Ltd.) was transformed by use of the ligation mixture. From the obtained ampicillin-resistant transformants, plasmid pGAI1 was isolated.

Figure 4:
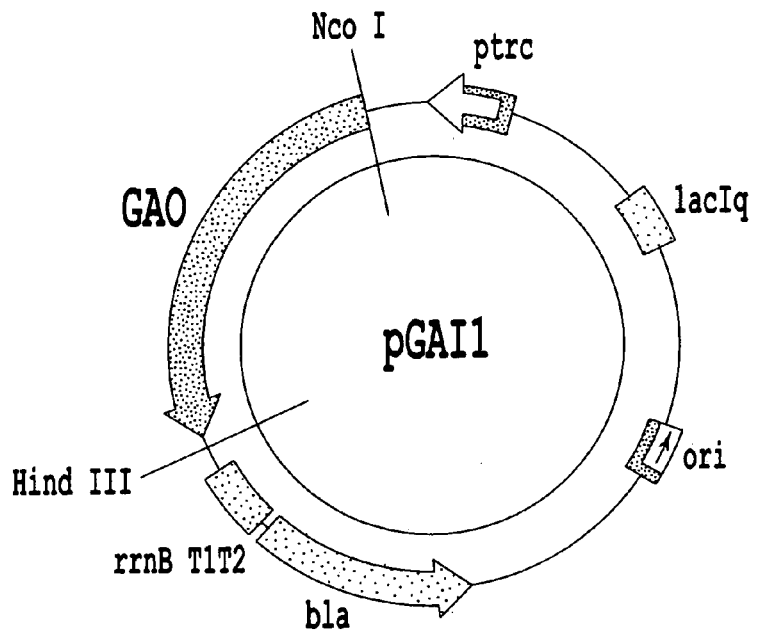
FIG. 4 shows the structure of plasmid pGAI1, wherein GAO represents an L-glutamate oxidase gene.
Figure 5A:
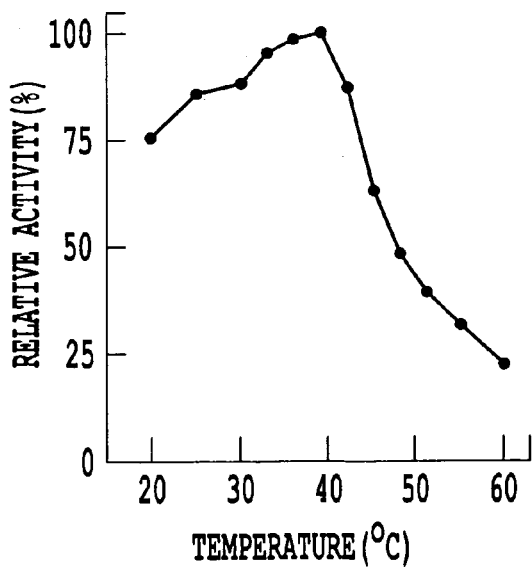
FIG. 5 shows optimum temperature ranges of L-glutamate oxidases according to the present invention and a *Streptomyces* sp. X-119-6 strain-derived L-glutamate oxidase, wherein (A) denotes L-glutamate oxidase fused with maltose binding protein (MBP) derived from *E. coli* JM109/pGOX mal1 (*E. coli* JM109/pGOX mal1-derived MBP-LGOX fusion protein); (B) denotes L-glutamate oxidase obtained by digesting a maltose binding protein by factor Xa (*E. coli* JM109/pGOX mal1-derived LGOX (factor Xa-treated); (C) denotes L-glutamate oxidase derived from *E. coli* JM109/pGAI1 (*E. coli* JM109/pGAI1-derived LGOX); and (D) denotes L-glutamate oxidase derived from *Streptomyces* sp. X-119-6 strain (LGOX derived from *Streptomyces* sp. X-119-6 strain).
Figure 5B:
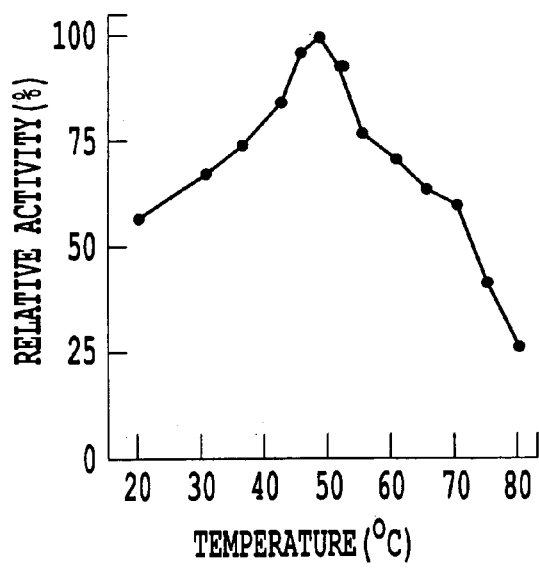
Figure 5C:
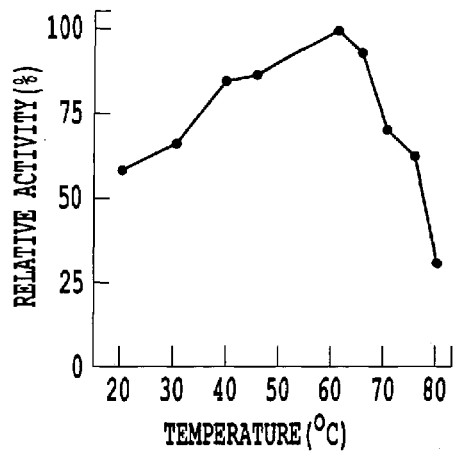
Figure 5D:
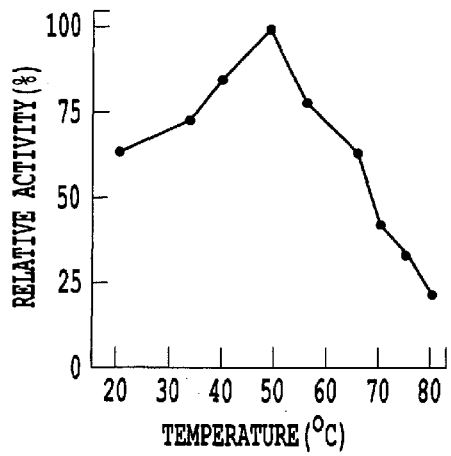

The plasmid pGAI1 is a product obtained by inserting into pTrc99A, at the NcoI-HindIII cleavage site downstream of the trc promotor, an NcoI-HindIII DNA fragment containing L-glutamate oxidase gene (GAO) derived from *Streptomyces* sp. X-119-6 (ATCC 39343) (FIG. 4). However, because of the addition of a initiation codon, N-terminal alanine is changed to methionine.

*E. coli* JM109 was transformed by use of the plasmid pGAI1, and the obtained transformant was inoculated into 2×TY medium (5 mL), for shaking-culture at 30° C. for about 12 hours. Subsequently, the culture product was inoculated into 2×TY medium (1 L) containing 20 g/L glucose, and then subjected to shaking culturing at 30° C. for about 18 hours. IPTG was added to the culture product, and the resultant mixture was cultured at the same temperature for about a further 6 hours. After completion of culturing, L-gultamate oxidase was isolated and purified according to the following purification method.

Purification method
(1) Collection, washing, and ultrasonication (100 W×15 minutes×2 times)
 ↓ (20 mM potassium phosphate buffer containing 100 mM NaCl)
(2) 20 to 80% Ammonium sulfate precipitation and dialysis
 ↓ (20 mM potassium phosphate buffer containing 100 mM NaCl)
(3) Ion exchange chromatography (stepwise elution by use of DEAE-Toyopearl 650M and 20 mM potassium phosphate buffer containing 100 to 200 mM NaCl)
 ↓
Condensation (Through Ultrafiltlation) and Dialysis
 ↓ (20 mM potassium phosphate buffer containing 100 mM NaCl)
(4) Ion exchange chromatography (gradient elution by use of DEAE-Toyopearl 650M and 20 mM potassium phosphate buffer containing 100 to 300 mM NaCl)

TABLE 2

| | Proteins (mg) | Activity (U) | Specific activity (U/mg protein) | Purity (fold) | Yield (%) |
|---|---|---|---|---|---|
| Crude enzyme solution | 1025 | 354.6 | 0.346 | 1 | 100 |
| Re-dissolved solution after ammonium sulfate precipitation | 282 | 139.7 | 0.495 | 1.43 | 39.4 |
| Solution after 1st ion exchange chromatography | 22.3 | 82.9 | 3.71 | 10.72 | 23.4 |
| Solution after 2nd ion exchange chromatography | 2.43 | 80.4 | 33.14 | 95.78 | 22.7 |

Example 4

Physicochemical Properties of L-glutamate Oxidase

A comparative study was performed with respect to the physicochemical properties of the following species of L-glutamate oxidase.
1) L-glutamate oxidase fused with maltose binding protein (MBP) derived from *E. coli* JM109/pGOX mal1 (may be referred to as *E. coli* JM109/pGOX mal1-derived MBP-LGOX fused protein)
2) L-glutamate oxidase which has undergone digesting of maltose binding protein with factor Xa (may be referred to as *E. coli* JM109/pGOX mal1-derived LGOX (after treatment with factor Xa))
3) L-glutamate oxidase derived from *E. coli* JM109/pGAI1 (may be referred to as *E. coli* JM109/pGAI1-derived LGOX)
4) L-glutamate oxidase derived from a strain *Streptomyces* sp. X-119-6 (may be referred to as *Streptomyces* sp. X-119-6-derived LGOX)

(1) Substrate Specificity

The species L-glutamate oxidase of 1) to 4) above were reacted with a variety of amino acids having concentrations of 8.2 mM or 32.8 mM. The results are shown in Tables 3 and 4.

TABLE 3

Substrate concentration: 8.2 mM

| Substrate | E. coli JM109/pGOX mal1-derived MBP-LGOX fusion protein | E. coli JM109/pGOX mal1-derived LGOX (after treatment with factor Xa) | E. coli JM109/pGAI1-derived LGOX | Streptomyces sp. X-119-6-derived LGOX |
|---|---|---|---|---|
| L-Glu | 100 | 100 | 100 | 100 |
| D-Glu | 0 | 0 | 0 | 0 |
| L-Gln | — | 0.07 | 0.09 | 0.11 |
| L-Asp | — | 0.66 | 0.65 | 0.54 |
| L-Asn | — | 0.58 | 0.66 | 0.61 |
| L-Ala | 0 | 0 | 0 | 0 |
| L-Leu | 0 | 0 | 0 | 0 |
| L-Ile | 0 | 0 | 0 | 0 |
| L-Met | 0 | 0 | 0 | 0 |
| L-Trp | 0 | 0 | 0 | 0 |
| L-Phe | 0 | 0 | 0 | 0 |
| L-Pro | 0 | 0 | 0 | 0 |
| Gly | 0 | 0 | 0 | 0 |
| L-Ser | 0 | 0 | 0 | 0 |
| L-Thr | 0 | 0 | 0 | 0 |
| L-Cys | 0 | 0 | 0 | 0 |
| L-Tyr | 0 | 0 | 0 | 0 |
| L-His | 0 | 0 | 0 | 0 |
| L-Arg | 0 | 0 | 0 | 0 |
| L-Lys | 0 | 0 | 0 | 0 |
| L-Cys acid | 0 | 0 | 0 | 0 |

—: Not measured
0: Not reacted at all

TABLE 4

Substrate concentration: 32.8 mM

| Substrate | E. coli JM109/pGOX mal1-derived MBP-LGOX fusion protein | E. coli JM109/pGOX mal1-derived LGOX (after treatment with factor Xa) | E. coli JM109/pGAI1-derived LGOX | Streptomyces sp. X-119-6-derived LGOX |
|---|---|---|---|---|
| L-Glu | 100 | 100 | 100 | 100 |
| D-Glu | 0 | 0 | 0 | 0 |
| L-Gln | 0.03 | 0.18 | 0.20 | 0.20 |
| L-Asp | 0.06 | 0.99 | 1.02 | 1.01 |
| L-Asn | 0.05 | 1.16 | 1.59 | 1.58 |
| L-Ala | 0 | 0 | 0 | 0 |
| L-Leu | 0 | 0 | 0 | 0 |
| L-Ile | 0 | 0 | 0 | 0 |
| L-Met | 0 | 0 | 0 | 0 |
| L-Trp | 0 | 0 | 0 | 0 |
| L-Phe | 0 | 0 | 0 | 0 |
| L-Pro | 0 | 0 | 0 | 0 |
| Gly | 0 | 0 | 0 | 0 |
| L-Ser | 0 | 0 | 0 | 0 |
| L-Thr | 0 | 0 | 0 | 0 |
| L-Cys | 0 | 0 | 0 | 0 |
| L-Tyr | 0 | 0 | 0 | 0 |
| L-His | 0 | 0 | 0 | 0 |
| L-Arg | 0 | 0 | 0 | 0 |
| L-Lys | 0 | 0 | 0 | 0 |
| L-Cys acid | 0 | 0 | 0 | 0 |

0: Not reacted at all

As is apparent from the above Tables, the L-glutamate oxidase of the present invention exhibits high specificity for L-glutamate.

(2) Other Physicochemical Properties

Figure 6A:
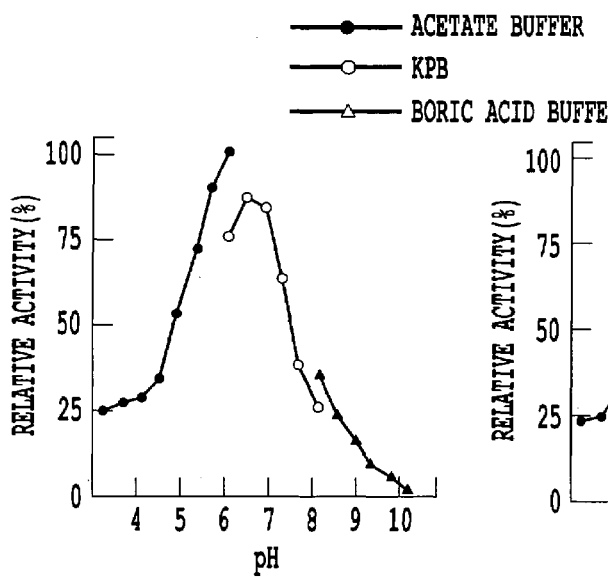
FIG. 6 shows optimum pH ranges of L-glutamate oxidases according to the present invention and a *Streptomyces* sp. X-119-6 strain-derived L-glutamate oxidase, wherein (A) denotes *E. coli* JM109/pGOX mal1-derived MBP-LGOX fusion protein; (B) denotes *E. coli* JM109/pGOX mal1-derived LGOX (factor Xa-treated); (C) denotes *E. coli* JM109/pGAI1-derived LGOX; and (D) denotes *Streptomyces* sp. X-119-6 strain-derived LGOX.
Figure 6B:
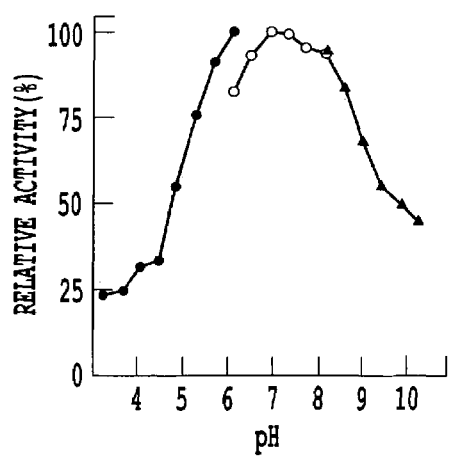

Results of assays for other physicochemical properties are shown in Table 5 and FIGS. 5 to 7. The assay conditions employed, described below, are modified ones of the above-described assays.

Optimal temperature: Reaction was performed at temperatures falling within the range of 20° C. to 80° C. (20° C. to 60° C. for *E. coli* JM109/pGOX mal1-derived MBP-LGOX fusion protein).

Optimal pH: The buffer employed is acetate buffer (pH 3.5 to 6.0), potassium phosphate buffer (pH 6.0 to 8.0), or borate buffer (pH 8.0 to 10.0).

Heat stability: Enzyme activity was determined after the reaction mixture was maintained at respective temperatures of 0° C. to 90° C. (pH 7.4, for 30 minutes)

TABLE 5

| Physicochemical properties | | | |
|---|---|---|---|
| | E. coli JM109/pGOX mal1-derived MBP-LGOX fusion protein | E. coli JM109/pGOX mal1-derived LGOX (after treatment with factor Xa) | E. coli JM109/pGAI1-derived LGOX |
| Optimal temp. | 20° C. to 45° C. | 20° C. to 70° C. | |
| Optimal pH | in the vicinity of pH 6.0–7.0 | in the vicinity of pH 6.0–8.5 | |
| Heat stability | stable up to 30° C. | stable up to 60° C. | |
| Km value with respect to L-glutamic acid | about 5.1 mM | about 0.2 mM | |
| Molecular weight and subunit structure | | 70,000 ± 6,000 (SDS-polyacrylamide gel electrophoresis) 140,000 ± 10,000 (gel permeation) Dimer of subunits having the same molecular weight of 70,000 ± 6,000 | |
| Coenzyme | Flavin adenine dinucleotide (FAD) | | | pH Stability: Enzyme activity was determined after the reaction mixture was maintained for 3 hours at 4° C. (at different pHs falling within the range of 3 to 10.5). As a result, both *Streptmyces* sp. X-119-6 strain-derived L-glutamate oxidase and *E. coli* JM109/pGAI1-derived L-glutamate oxidase were found to be stable at pHs between 5.5 and 10.5.

INDUSTRIAL APPLICABILITY

The L-glutamate oxidase of the present invention, different from those previously reported, is a novel enzyme formed of two identical subunits each having a molecular weight of about 70 kD. The L-glutamate oxidase of the present invention is capable of producing L-glutamate oxidase conveniently and inexpensively when the gene of the specified enzyme is subjected to a recombinant gene technique by use of a transformant such as *E. coli*.

The invention claimed is:

1. An isolated polynucleotide encoding a protein consisting of the amino acid sequence of SEQ ID NO: 1, wherein said protein has L-glutamate oxidase activity.

2. The polynucleotide according to claim 1, which has the nucleotide sequence of SEQ ID NO: 2.

3. The polynucleotide according to claim 1, wherein said polynucleotide is isolated from a microorganism belonging to *Streptomyces*.

4. An isolated polynucleotide that hybridizes to the polynucleotide according to claim 2 or to the complement thereof under stringent conditions and which encodes a protein having an L-glutamate oxidase activity, wherein said stringent conditions comprise hybridization at 60° C. in a solution comprising 5×SSC, 0.1 % w/v N-lauroylsarcosine sodium salt, 0.02% w/v SDS, and 0.5% w/v blocking reagent.

5. The polynucleotide according to claim 4, wherein said polynucleotide is isolated from a microorganism belonging to *Streptomyces*.

6. An expression vector comprising the polynucleotide according to claim 1.

7. A method for producing an L-glutamate oxidase, comprising transforming a host microorganism with an expression vector according to claim 6 culturing the resultant transformant, to thereby produce L-glutamate oxidase isolating the L-glutamate oxidase from the cultured product; and purifying the L-glutamate oxidase.

8. The method for producing an L-glutamate oxidase according to claim 7, wherein the host microorganism is *E. coli*.

9. The polynucleotide according to claim 2, wherein said polynucleotide is isolated from a microorganism belonging to *Streptomyces*.

10. An expression vector comprising the polynucleotide according to claim 2.

11. An expression vector comprising the polynucleotide according to claim 4.

12. A method for producing an L-gtutamate oxidase, comprising transforming a host microorganism with an expression vector according to claim 11; culturing the resultant transformant, to thereby produce L-glutamate oxidase isolating the L-glutamate oxidase from the cultured product; and purifying the L-glutamate oxidase.

13. The method for producing an L-glutamate oxidase according to claim 12, wherein the host microorganism is *E. coli*.

* * * * *

SEQUENCE LISTING

<160> NUMBER OF SEQ ID NOS: 10

<210> SEQ ID NO 1
<211> LENGTH: 687
<212> TYPE: PRT
<213> ORGANISM: Streptomyces sp.

<400> SEQUENCE: 1

```
Ala Asn Glu Met Thr Tyr Glu Gln Leu Ala Arg Glu Leu Leu Leu Val
1               5                   10                  15

Gly Pro Ala Pro Thr Asn Glu Asp Leu Lys Leu Arg Tyr Leu Asp Val
            20                  25                  30

Leu Ile Asp Asn Gly Leu Asn Pro Pro Gly Pro Pro Lys Arg Ile Leu
        35                  40                  45

Ile Val Gly Ala Gly Ile Ala Gly Leu Val Ala Gly Asp Leu Leu Thr
    50                  55                  60

Arg Ala Gly His Asp Val Thr Ile Leu Glu Ala Asn Ala Asn Arg Val
65                  70                  75                  80

Gly Gly Arg Ile Lys Thr Phe His Ala Lys Lys Gly Glu Pro Ser Pro
                85                  90                  95

Phe Ala Asp Pro Ala Gln Tyr Ala Glu Ala Gly Ala Met Arg Leu Pro
            100                 105                 110

Ser Phe His Pro Leu Thr Leu Ala Leu Ile Asp Lys Leu Gly Leu Lys
        115                 120                 125

Arg Arg Leu Phe Phe Asn Val Asp Ile Asp Pro Gln Thr Gly Asn Gln
    130                 135                 140

Asp Ala Pro Val Pro Val Phe Tyr Lys Ser Phe Lys Asp Gly Lys
145                 150                 155                 160

Thr Trp Thr Asn Gly Ala Pro Ser Pro Glu Phe Lys Glu Pro Asp Lys
                165                 170                 175

Arg Asn His Thr Trp Ile Arg Thr Asn Arg Glu Gln Val Arg Arg Ala
            180                 185                 190

Gln Tyr Ala Thr Asp Pro Ser Ser Ile Asn Glu Gly Phe His Leu Thr
        195                 200                 205

Gly Cys Glu Thr Arg Leu Thr Val Ser Asp Met Val Asn Gln Ala Leu
    210                 215                 220

Glu Pro Val Arg Asp Tyr Tyr Ser Val Lys Gln Asp Asp Gly Thr Arg
225                 230                 235                 240

Val Asn Lys Pro Phe Lys Glu Trp Leu Ala Gly Trp Ala Asp Val Val
                245                 250                 255

Arg Asp Phe Asp Gly Tyr Ser Met Gly Arg Phe Leu Arg Glu Tyr Ala
            260                 265                 270

Glu Phe Ser Asp Glu Ala Val Glu Ala Ile Gly Thr Ile Glu Asn Met
        275                 280                 285

Thr Ser Arg Leu His Leu Ala Phe Phe His Ser Phe Leu Gly Arg Ser
    290                 295                 300

Asp Ile Asp Pro Arg Ala Thr Tyr Trp Glu Ile Glu Gly Gly Ser Arg
305                 310                 315                 320

Met Leu Pro Glu Thr Leu Ala Lys Asp Leu Arg Asp Gln Ile Val Met
                325                 330                 335

Gly Gln Arg Met Val Arg Leu Glu Tyr Tyr Asp Pro Gly Arg Asp Gly
            340                 345                 350

His His Gly Glu Leu Thr Gly Pro Gly Gly Pro Ala Val Ala Ile Gln
```

-continued

```
          355                 360                 365
Thr Val Pro Glu Gly Glu Pro Tyr Ala Ala Thr Gln Thr Trp Thr Gly
        370                 375                 380

Asp Leu Ala Ile Val Thr Ile Pro Phe Ser Ser Leu Arg Phe Val Lys
385                 390                 395                 400

Val Thr Pro Pro Phe Ser Tyr Lys Lys Arg Arg Ala Val Ile Glu Thr
                405                 410                 415

His Tyr Asp Gln Ala Thr Lys Val Leu Leu Glu Phe Ser Arg Arg Trp
            420                 425                 430

Trp Glu Phe Thr Glu Ala Asp Trp Lys Arg Glu Leu Asp Ala Ile Ala
        435                 440                 445

Pro Gly Leu Tyr Asp Tyr Tyr Gln Gln Trp Gly Glu Asp Asp Ala Glu
    450                 455                 460

Ala Ala Leu Ala Leu Pro Gln Ser Val Arg Asn Leu Pro Thr Gly Leu
465                 470                 475                 480

Leu Gly Ala His Pro Ser Val Asp Glu Ser Arg Ile Gly Glu Glu Gln
                485                 490                 495

Val Glu Tyr Tyr Arg Asn Ser Glu Leu Arg Gly Gly Val Arg Pro Ala
            500                 505                 510

Thr Asn Ala Tyr Gly Gly Gly Ser Thr Thr Asp Asn Pro Asn Arg Phe
        515                 520                 525

Met Tyr Tyr Pro Ser His Pro Val Pro Gly Thr Gln Gly Gly Val Val
    530                 535                 540

Leu Ala Ala Tyr Ser Trp Ser Asp Asp Ala Ala Arg Trp Asp Ser Phe
545                 550                 555                 560

Asp Asp Ala Glu Arg Tyr Gly Tyr Ala Leu Glu Asn Leu Gln Ser Val
                565                 570                 575

His Gly Arg Arg Ile Glu Val Phe Tyr Thr Gly Ala Gly Gln Thr Gln
            580                 585                 590

Ser Trp Leu Arg Asp Pro Tyr Ala Cys Gly Glu Ala Ala Val Tyr Thr
        595                 600                 605

Pro His Gln Met Thr Ala Phe His Leu Asp Val Val Arg Pro Glu Gly
    610                 615                 620

Pro Val Tyr Phe Ala Gly Glu His Val Ser Leu Lys His Ala Trp Ile
625                 630                 635                 640

Glu Gly Ala Val Glu Thr Ala Val Arg Ala Ala Ile Ala Val Asn Glu
                645                 650                 655

Ala Pro Val Gly Asp Thr Gly Val Thr Ala Ala Gly Arg Arg Gly
            660                 665                 670

Ala Ala Ala Ala Thr Glu Pro Met Arg Glu Glu Ala Leu Thr Ser
        675                 680                 685
```

<210> SEQ ID NO 2
<211> LENGTH: 2061
<212> TYPE: DNA
<213> ORGANISM: Streptomyces sp.

<400> SEQUENCE: 2

| | |
|---|---|
| gccaacgaga tgacctacga gcagctggcc cgcgaactgc tgctggtcgg ccccgcgccc | 60 |
| accaacgagg acctcaagct gcggtacctc gacgtgctga tcgacaacgg actcaatccc | 120 |
| cccggaccgc ccaagcgcat cctgatcgtc ggcgccggta tcgccggcct ggtcgccggt | 180 |
| gacctgctga cccgcgccgg acacgacgtg acgatcctgg aggccaacgc caacccgggtc | 240 |
| ggcgggcgga tcaagacctt ccacgccaag aagggcgagc cgtcgccgtt cgccgacccc | 300 |

-continued

```
gcgcagtacg cggaggcggg cgcgatgcgc ctgcccagct tccacccgct gaccctggcg    360
ctgatcgaca aactcggcct gaagcgacgg ctgttcttca acgtcgacat cgatccgcag    420
accggcaacc aggacgcgcc ggtcccccg gtgttctaca agtcgttcaa ggacggcaag     480
acctggacca acggcgcgcc cagcccggag ttcaaggagc cggacaagcg caaccacacc    540
tggatccgca ccaaccgcga gcaggtgcgg cgcgcccagt acgccacgga cccctccagc    600
atcaacgagg gcttccacct caccggctgc gagacccggc tgaccgtctc ggacatggtc    660
aaccaggcgc tggagccggt gcgcgactac tactccgtga agcaggacga cggaacgcgg    720
gtcaacaagc cgttcaagga atggctggcg ggctgggccg acgtcgtccg cgacttcgac    780
ggctattcga tggggcgctt cctgcgcgag tacgcggagt tcagcgacga ggccgtcgag    840
gcgatcggca ccatcgagaa catgacctcg cgcctccacc tggcgttctt ccacagcttc    900
ctggggcgca gcgacatcga cccccgcgcc acgtactggg agatcgaggg cggcagccgc    960
atgctgccgg aaacgctggc caaggacctg cgggaccaga tcgtgatggg ccagcgaatg   1020
gtgcggctgg agtactacga ccccggccgc gacgggcacc acggcgaact caccggtccc   1080
ggcggaccgg ccgtcgccat ccagaccgtc cccgagggcg aaccgtacgc ggcgacccag   1140
acctggaccg gtgacctggc gatcgtcacc atcccgttct ccagcctgcg gttcgtcaag   1200
gtgaccccgc cgttctcgta caagaagcgc cgcgccgtca tcgagaccca ctacgaccag   1260
gccaccaagg tgctgctgga gttctcgcgg cgctggtggg agttcaccga ggcggactgg   1320
aagcgggagc tggacgcgat cgcaccgggt ctgtacgact actaccagca gtggggcgag   1380
gacgacgccg aggccgcgct ggcccttccg cagagcgtcc gcaacctgcc caccgggctg   1440
ctgggcgcgc atccgagcgt ggacgagagc cggatcggcg aggagcaggt ggagtactac   1500
cgcaactccg agctgcgcgg cggggtgcgg ccggccacca acgcctacgg cggcggttcc   1560
accaccgaca accccaaccg cttcatgtac tacccctccc acccggtgcc cgggacccag   1620
ggcggtgtgg tgctggccgc ctactcctgg tcggacgacg ccgcccgctg ggactccttc   1680
gacgacgccg agcgctacgg ctacgccctg gagaacctcc agtcggtgca cggccgccgg   1740
atcgaggtct tctacaccgg cgccggccag acccagagtt ggctgcgcga cccgtacgcg   1800
tgcgagagag cggcggtcta cacccgcac cagatgaccg ccttccacct cgacgtggtc    1860
cggcccgagg ggccggtgta cttcgccggt gagcacgtgt cgctgaagca cgcctggatc   1920
gagggagcgg tggaaaccgc cgtacgggcc gccatcgccg tcaacgaggc acccgtgggg   1980
gacacgggcg tcaccgcggc cgccggtcgc cgcggggccg ccgcggcaac ggaaccgatg   2040
cgagaggaag cactgacgtc a                                             2061
```

<210> SEQ ID NO 3
<211> LENGTH: 7
<212> TYPE: PRT
<213> ORGANISM: Streptomyces sp

<400> SEQUENCE: 3

Ala Asn Glu Met Thr Tyr Glu
1               5

<210> SEQ ID NO 4
<211> LENGTH: 7
<212> TYPE: PRT
<213> ORGANISM: Streptomyces sp

<400> SEQUENCE: 4

```
Ala Ile Val Thr Ile Pro Phe
1               5
```

```
<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
aacgagatga cstacgagca                                          20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gcsatcgtsa csatcccstt                                          20

<210> SEQ ID NO 7
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ccacaccggg gccgaattca tgaaccgaga t                             31

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
aggtactcgg ccaccctgca ggtc                                     24

<210> SEQ ID NO 9
<211> LENGTH: 54
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gcgccatgga ggaattcgcg catgaacgag atgacctacg agcagctggc ccgc    54

<210> SEQ ID NO 10
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
gcgaagcttg atcatgacgt cagtgcttcc tctcgcatc                     39
```